United States Patent [19]

Cummings

[11] Patent Number: 4,490,510

[45] Date of Patent: Dec. 25, 1984

[54] EPOXY CURING AGENTS, METHOD FOR MAKING THEM, METHOD OF CURING EPOXY RESINS, AND CURED EPOXY RESINS

[76] Inventor: Lowell O. Cummings, 133 Crane Dr., San Anselmo, Calif. 94960

[21] Appl. No.: 396,319

[22] Filed: Jul. 8, 1982

[51] Int. Cl.$^3$ .............................................. C08L 61/24
[52] U.S. Cl. .................................. 525/490; 525/510
[58] Field of Search ....................... 525/490, 510, 513

[56] References Cited

U.S. PATENT DOCUMENTS

| | | | |
|---|---|---|---|
| 2,786,823 | 3/1957 | Keim | 525/509 |
| 2,786,824 | 3/1957 | Keim | 525/509 |
| 2,786,826 | 3/1957 | Keim | 525/509 |
| 2,806,826 | 9/1957 | Squire | 525/509 |
| 2,828,276 | 3/1958 | De Groote et al. | 525/490 |
| 2,864,790 | 12/1958 | De Groote et al. | 525/490 |
| 2,864,796 | 12/1958 | De Groote et al. | 525/490 |
| 3,309,341 | 3/1967 | Abrahams et al. | 525/509 |
| 3,931,110 | 1/1976 | Freeman et al. | 525/490 |
| 4,018,740 | 5/1977 | Kruglikov et al. | 525/509 |

*Primary Examiner*—John C. Bleutge
*Assistant Examiner*—Robert E. L. Sellers
*Attorney, Agent, or Firm*—Owen, Wickersham & Erickson

[57] ABSTRACT

A new class of epoxy curing agents has been discovered that utilizes the monomer of (a) urea-formaldehyde, (b) phenol modified urea-formaldehyde, or (c) thiourea-formaldehyde as the center of a polyamine molecule. The ether monomers are reacted with conventional aliphatic, cycloaliphatic, and aromatic polyamines to split off alcohol and water-yielding urea-formaldehyde etc., polyamine epoxy curing agents. Epoxy resins can be readily cured and, with some curing agents, under water, giving new cured epoxy resins.

47 Claims, No Drawings

EPOXY CURING AGENTS, METHOD FOR MAKING THEM, METHOD OF CURING EPOXY RESINS, AND CURED EPOXY RESINS

This invention relates to novel compounds useful as epoxy curing agents, to a method for making these new compounds, to a novel method of curing epoxy resins, and to novel cured epoxy resins.

A new class of epoxy curing agents has been discovered that utilizes the structure of urea-formaldehyde and also the structure of phenol-modified urea-formaldehyde as the center of a polyamine molecule. The amine groups are arranged around the urea-formaldehyde center in a radial fashion.

This may be represented as:

$$\begin{array}{c} X^1CH_2 \\ \phantom{X^1CH_2} \diagdown \\ \phantom{XXX} N-C-N \\ \phantom{X^1CH_2} \diagup \phantom{XX} \| \phantom{XX} \diagdown \\ X^1CH_2 \phantom{XXXX} O \phantom{XXXX} CH_2X^2 \end{array} \begin{array}{c} CH_2X^1 \\  \\  \\  \end{array}$$

where $X^1$ is $$HN-R^1-N-$$
$$\phantom{HN-}|\phantom{R^1-}|$$
$$\phantom{HN-}R^2\phantom{-}R^3$$

and $X^2$ is either identical to $X^1$ or is

[structure: phenol ring with OH, $CH_2X^1$, and $R^4$ substituents]

$R^1$, $R^2$, $R^3$, and $R^4$ are defined below.

This structure has a low amount of steric hindrance; that is, the structure of the molecule allows the most space between its components. This provides easy access for an epoxy molecule to react with these widely spaced amine groups.

The structures of these new compounds give a high degree of cross linking when reacted with epoxy resins and, therefore, contribute to the toughness and strength of the cured amine-epoxy resin.

Another advantage of incorporation of the urea-formaldehyde structure in the polyamine curing agent is that the curing agent is water-white in color, and so the subsequently cured amine-epoxy resin can be water-white. Urea-formaldehyde resins themselves are intrinsically colorless and resist becoming yellowish, and this same resistance to yellowing can be incorporated in the urea-formaldehyde polyamine structure.

The phenol-modified urea-formaldehyde resins have some yellowness, but are quite light.

Both the urea-formaldehyde polyamines and the phenol-modified urea-formaldehyde polyamines can be low in cost, because urea, formaldehyde, and phenol are low-cost raw materials, and so are many of the polyamines.

Success in manufacturing these urea-formaldehyde polyamine curing agents depends, in part, on employing a process of urea-formaldehyde synthesis that produces largely monomeric urea-formaldehyde ether molecules.

One successful method of making urea-formaldehyde ether monomers is to react urea and paraformaldehyde in a low-molecular-weight alcohol, such as methanol at a ratio of urea molecules to formaldehyde molecules of one to four. This results in the following general structure:

$$\begin{array}{c} R-O-CH_2 \phantom{XXX} O \phantom{XXX} CH_2-O-R \\ \phantom{XXX} \diagdown \phantom{XXX} \| \phantom{XXX} \diagup \\ \phantom{XXXXX} N-C-N \\ \phantom{XXXXX} | \phantom{XXX} | \\ \phantom{XXXXX} CH_2 \phantom{X} CH_2 \\ \phantom{XXXXXX} \diagdown \diagup \\ \phantom{XXXXXXX} O \end{array}$$

ether of methylol group     uron structure     ether of methylol group
(an ether of two methylol groups)

Here, R is a methyl, ethyl, propyl, or butyl radical.

Once this monomeric urea-formaldehyde ether molecule has been synthesized, it can be reacted directly with any of a number of polyamines including those that are presently utilized in the manufacture of amine curing agents.

A fundamental discovery of this patent is the discovery that polyamines split the ether groups of the above urea-formaldehyde molecule. Then, one of the amine groups of the polyamine forms a carbon-nitrogen bond at the side of the ether splitting, giving off the reaction products of alcohol and water. For example:

$$4X^1\text{-polyamine} + \begin{array}{c} R^5-O-CH_2 \phantom{XX} O \phantom{XX} CH_2-O-R^5 \\ \diagdown \phantom{XX} \| \phantom{XX} \diagup \\ N-C-N \\ | \phantom{XXX} | \\ CH_2 \phantom{X} CH_2 \\ \diagdown \diagup \\ O \end{array} \longrightarrow$$

$$\begin{array}{c} X^1CH_2 \phantom{XX} O \phantom{XX} CH_2X^1 \\ \diagdown \phantom{XX} \| \phantom{XX} \diagup \\ N-C-N \\ \diagup \phantom{XXXX} \diagdown \\ X^1CH_2 \phantom{XXXX} CH_2X^1 \end{array} + 2R^5OH + H_2O.$$

$R^5$ is a lower alkyl radical, having one to four carbon atoms.

This ease of splitting of these ether groups is somewhat surprising, because I had earlier found that the corresponding ether groups in a melamine formaldehyde resin are not split, under the same conditions.

As stated above, $X^1$ may be generalized as $$HN-R^1-N-$$
$$\phantom{HN-}|\phantom{R^1-}|$$
$$\phantom{HN-}R^2\phantom{-}R^3$$

The following table shows the complete grouping of these radicals that can be $R^1$.

| | CHART FOR R¹ | |
|---|---|---|
| | Name of Polyamine Used to React with U-F Monomer, etc. | R¹ |
| (a) | diethylene triamine | $-CH_2-CH_2-\overset{H}{\underset{|}{N}}-CH_2-CH_2-$ |
| (b) | triethylene tetramine | $-CH_2-CH_2-\overset{H}{\underset{|}{N}}-CH_2-CH_2-\overset{H}{\underset{|}{N}}-CH_2-CH_2-$ |
| (c) | hexamethylene diamine | $-CH_2-CH_2-CH_2-CH_2-CH_2-CH_2-$ |
| (d) | polyoxypropylene diamines<br>X = 2.6 has M.W. (molecular weight) of 230 approx.<br>X = 5.6 has M.W. (molecular weight) of 400 approx.<br>Commercial Name:<br>Jeffamine D-230<br>Jeffamine D-400<br>Texaco Chemical Co. | $-CH(CH_3)-CH_2[-O-CH_2-CH(CH_3)]_{\overline{X}}$ |
| (e) | polyoxypropylene triamine<br><br>X + Y + Z = 5.3<br>M.W. of 400<br>Commercial Name:<br>Jeffamine T-403 | $\begin{array}{c}CH_2[OCH_2CH(CH_3)]_{\overline{X}}\\|\\CH_3CH_2C-CH_2[OCH_2CH(CH_3)]_Y-NH_2\\|\\CH_2[OCH_2CH(CH_3)]_{\overline{Z}}\end{array}$ |
| (f) | poly(oxyethylene)diamine<br><br>b = 13.5<br>a + c = 3.5<br>M.W. of 600<br>Commercial Name:<br>Jeffamine ED diamine | $-\overset{CH_3}{\underset{|}{C}}HCH_2(OCHCH_2)_a(OCH_2CH_2)_b(OCH_2\overset{CH_3}{\underset{|}{C}}H)_c-$ |
| (g) | trimethyl hexamethylene diamine | $-CH_2-\overset{CH_3}{\underset{\underset{CH_3}{|}}{\overset{|}{C}}}-CH_2-\overset{CH_3}{\underset{|}{C}}H-CH_2-CH_2-$ |
| (h) | N—aminoethyl piperazine | 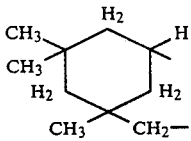 |
| (i) | 1,5 aminomethyl pentane diamine | $-CH_2CH_2CH_2CH_2\overset{|}{C}HCH_3$ |
| (j) | isophorone diamine | 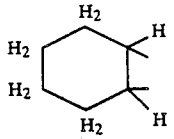 |
| (k) | 1,2-diamine cyclohexane | (cyclohexane with H₂, H₂, H₂, H₂ and H, H) |
| (l) | xylene diamine | 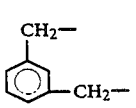 |

| | CHART FOR R¹ -continued | |
|---|---|---|
| | Name of Polyamine Used to React with U-F Monomer, etc. | R¹ |
| (m) | 2,4-Bis(p-amino benzyl)aniline an aromatic polyamine | 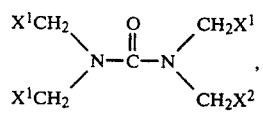 |
| (n) | mixture of BABA (du Pont), mixture principally of methylene dianiline and 2,4 bis(p-amino benzyl)aniline | 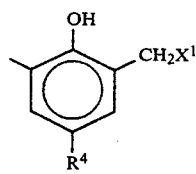 |
| (o) | oleyl diamine | —CH₂—CH₂—CH₂— |

For all of the amines (a) through (n) in the above table, $R^2$ and $R^3$ are both H. For the oleyl diamine, amine (o), either $R^2$ or $R^3$, but not both, is $C_{18}H_{35}$ and the other one is again H.

In the formula $$\begin{array}{c} X^1CH_2 \quad O \quad CH_2X^1 \\ \diagdown \quad \| \quad \diagup \\ N-C-N \\ \diagup \quad \quad \diagdown \\ X^1CH_2 \quad \quad CH_2X^2 \end{array}$$

$X^1$ is as defined above, while $X^2$ may either be identical to $X^1$ or may be

[structure: phenol with OH, CH₂X¹ substituent, and R⁴]

where $R^4$ is hydrogen or an alkyl radical with one to nine carbon atoms.

There are amine curing agents on the market that are made from phenol, formalin (a water solution of formaldehyde) and a polyamine. These have no relationship to the urea-formaldehyde polyamines of the present invention because they are made by a different chemical route, and have vastly different properties. The manufacture of these phenol-formaldehyde amines is illustrated by Product Data Sheet 22-E-370-2-6 published by Veba-Chemi AG of Germany, which describes the reacting of phenol and 36% formalin using a basic catalyst. The polyamine is added to this water solution of the phenol-formaldehyde resin, and subsequently the water is driven off, resulting in a yellow viscous liquid.

As stated earlier, this resin is in no way related to the urea-formaldehyde polyamines of this invention, for no ether groups are formed in the water solution of phenol and formaldehyde under the above-stated basic conditions.

The urea-formaldehyde ether monomers are made in an alcohol medium. The urea, paraformaldehyde (a solid form or polymer of formaldehyde having typically 91% formaldehyde content), and an alcohol, such as methanol, are first subjected to basic conditions under low heat such as 50° C. This brief alkaline reaction causes the paraformaldehyde to dissolve. Then the reaction is made strongly acidic, e.g., a pH of 2; at this time an exotherm takes place, as a result of the formation of ether groups, for ethers of urea-formaldehyde are only formed under acid conditions. The reaction is held at 70°-80° C. for a time in the order of one hour, to insure good ether formation. The monomer reaction is then finished by bringing the pH to 7.0.

There may be small amounts of methylol groups in these urea-formaldehyde monomers. These methylol groups react with the polyamine in the same manner as the ethers react.

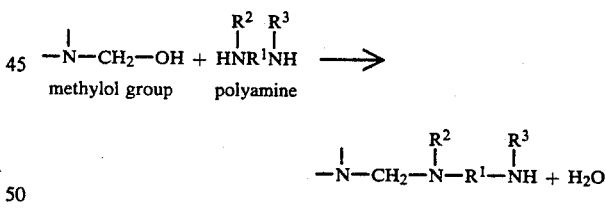

The formation of ether groups in the urea-formaldehyde resin can be followed by infrared spectrophotometry analysis. A sample of the reaction is scanned in an infrared spectroscopy instrument. The ether groups in urea-formaldehyde are shown by an infrared peak at 9.3 microns (1075 cm⁻¹). See the book *An Infrared Spectroscopy Atlas for the Coatings Industry*, 1980, Federation of Societies for Coating Technology, page 33.

This 9.3 micron peak develops soon after acidic conditions are made. The final urea-formaldehyde ether monomer has a very large 9.3 micron ether peak at the end of the reaction.

The progress of the reaction of the urea-formaldehyde ether monomer with the polyamine can be followed by noting that the ether peak is destroyed very soon after the urea-formaldehyde ether monomer is added to the polyamine. The finished reaction product has no trace of this 9.3 micron peak. The mixing of the urea-formaldehyde ether monomer into the polyamine is generally done at low temperature, such as 25° C. An exotherm takes place during the mixing which raises the temperature some 30° C. Then the alcohol and water of reaction are distilled off giving typically a water white, low viscosity, transparent liquid with remarkably good epoxy curing properties.

Some specific examples illustrate the formation of the urea-formaldehyde ether and related monomers and the reaction of the monomers with polyamines.

EXAMPLE 1

Urea-Formaldehyde Ether Monomer in Methanol

In a three liter glass flask fitted with a stainless steel paddle stirrer, thermometer, a pH electrode and a reflux condenser, is charged:
 1200 g. methyl alcohol 99%
 1200 g. 91% flake paraformaldehyde (corresponding to 1092 g. of 100% $CH_2O = 36.4$ moles)
 540 g. urea = 9 moles.

This mix was stirred and heated to 40° C. The pH of this mix was 3.0. The pH was brought to 10.5 by the addition of a small amount of 40% sodium hydroxide. As the temperature rose to 55° C., the paraformaldehyde and the urea were dissolved, making a clear solution. At this point 50% $H_2SO_4$ was added to bring the pH to 2.5. This caused a mild exotherm, bringing the temperature to 78° C. The pH was maintained at 2.0–2.5, and the temperature was maintained at about 80° C. for about forty minutes. Then the pH was brought to 7.0 with NaOH. The cooled urea-formaldehyde solution had suspended $Na_2SO_4$ in it, which was filtered out leaving a water-white, transparent, low-viscosity liquid containing about 55% non-volatile urea-formaldehyde ether monomer. Infrared analysis showed a strong peak at 9.3 microns, indicating ethers of methylol groups.

EXAMPLE 2

Thiourea-Formaldehyde Ether Monomer in Methanol

It has been found that thiourea

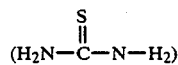

readily reacts in the same manner as urea in making the monomer.

In a 500 ml. flask fitted with a stainless steel paddle stirrer, thermometer, a pH electrode and reflux condenser, was charged:
 One mole, 76 g. thiourea, crystals, 99%
 Four moles, 132 g. 91% flake paraformaldehyde (corresponding to 120 g. of 100% $CH_2O$) 200 g. methyl alcohol 99%.

This mix was stirred and heated to about 40° C. The pH of this mix was 5.2. The pH was brought to 11.1 by the addition of a small amount of 40% sodium hydroxide. As the temperature rose to 60° C., the paraformaldehyde and thiourea dissolved making a clear solution. At this point 50% $H_2SO_4$ was added to bring the pH to 2.5. This caused a mild exotherm bringing the temperature to 70° C. This mix was stirred for one hour maintaining the temperature at 65° to 70° C.

During this time the pH spontaneously fell to 1.65. Then the pH was brought to 7.0 with NaOH. The cooled thiourea-formaldehyde solution had suspended $Na_2SO_4$ in it, which was filtered out leaving a water-white, transparent low-viscosity liquid containing about 48% non-volatile thiourea-formaldehyde ether monomer.

EXAMPLE 3

Composite Urea-Nonyl-Phenol Formaldehyde Ether Monomer

In a 500 ml. glass flask fitted with a stainless steel paddle stirrer, thermometer, pH electrode, and reflux condenser, the following ingredients were added:
 0.5 mole, 110 g. nonyl phenol
 0.5 mole, 30 g. urea
 3.03 mole, (100 g. of 91% paraformaldehyde corresponding to 91 g. 100% $CH_2O$) 250 g. isopropyl alcohol, 99%.

This mix was heated and stirred while 40% NaOH was added to bring the pH from 2.5 to 11.0. At 85° C. the paraformaldehyde and urea were dissolved to make a clear solution. Then 50% $H_2SO_4$ was added to bring the pH to 1.2. A mile exotherm took place, causing some refluxing. The temperature was maintained at about 70° C. for an hour while the pH was held at or near 1.2. Then NaOH was used to bring the pH to 7.0. The filtered solution was a light yellow transparent solution containing about 47% urea-nonyl phenol formaldehyde ether monomer. A large infrared peak at 9.3 microns indicated ethers of methylol groups.

EXAMPLE 4

Composite Urea-Phenol Formaldehyde Ether Monomer

In a one liter glass flask fitted with a stainless steel paddle stirrer, thermometer, pH electrode and reflux condenser, the following ingredients were added:
 300 g. methyl alcohol 99%
 2 moles, 188 g. phenol, U.S.P.
 1 mole, 60 g. urea
 3 moles, 99 g. 91% paraformaldehyde, (corresponding to 90 g. 100% $CH_2O$).

The mix was stirred and heated while 40% NaOH was added to bring the pH from 6.5 to 9.5. At 50° C. the paraformaldehyde dissolved, forming a transparent, slightly yellow liquid. Then 50% $H_2SO_4$ was added to bring the pH to 2.1. An exotherm took place, bringing the temperature from 52° to 68° C. The pH dropped to 1.0. The temperature was maintained at 64° C. for ten minutes and the pH was brought from 1.0 to 7.0 with NaOH.

The cooled solution had some white precipitate which was filtered off, leaving a water-white, transparent solution. Infrared analysis showed a strong urea carbonyl peak at 6.05 microns and a large ether peak at 9.3 microns. The solution had about 50% non-volatile urea-phenol formaldehyde ether monomer.

EXAMPLE 5

Urea-Formaldehyde Ether Monomer Reacted with an Aromatic Polyamine

The urea-formaldehyde ether monomer of Example 1, in an amount of 85 grams (47.5 grams of non-volatiles, i.e., 1 equivalents), is reacted with 1 mole (304 grams) of du Pont BABA, having a composition, weight percent:
 p,p-methylene dianiline: 3–10%
 2,4-bis(p-aminobenzyl) aniline (triamine): 70–80%
 tetramine: 10–80%
 higher amines: 1.

The aromatic polyamine was heated and stirred in a flask to 100° C. and the urea-formaldehyde ether monomer was added over 20 min. time and the temperature had climbed to 125° C.

Then 50 g. of benzyl alcohol was added to reduce the viscosity of this thick red brown liquid with a whitish crust on top. Methanol was distilled off during this time. Subsequently the whitish crust was dispersed in the red brown liquid and the crust dissolved into the main liquid giving a transparent viscous liquid at 150° C.

This liquid solidified as a dark red-brown brittle solid at about 90° C., considerably higher than the starting polymethylene dianiline. There was a urea carbonyl peak shown in infrared analysis of the final product at about 6.05 microns. This was not present in the starting polymethylene dianiline. The infrared peak at 6.05 microns indicated that a compound had been formed between the polymethylene dianiline and the urea-formaldehyde ether monomer.

EXAMPLES OF THE REACTION OF THE UREA-FORMALDEHYDE AND RELATED ETHER MONOMERS WITH POLYAMINES

All reactions were done in a glass flask fitted with paddle stirrer, thermometer, addition funnel and a distillation condenser. In all cases the polyamine was stirred in the flask at room temperature, while the urea-formaldehyde ether or related monomer solution in alcohol was added to the polyamine. If the opposite addition were done,—i.e., adding the polyamine to the urea-formaldehyde ether solution—a gel would result in a short time. A substantial exotherm results from the addition of the monomer solution etc. to the polyamine during the ten to twenty minutes addition time. Slow addition is important, for too-rapid addition can result in some gel particles.

After the addition of the monomer was complete, alcohol and water were distilled off from the urea-formaldehyde polyamine or related polyamine. Some distillations were at atmospheric pressure where the residue temperature was 130° C. Other distillations were done under reduced pressure of about 25 inches of vacuum where the temperature was 75° C.

In the following table urea-formaldehyde ether, is abbreviated to UF, urea-formaldehyde ether monomer to UFM, and urea-phenol-substituted-formaldehyde ether to UPFM.

TABLE 1

| Example No. | UFM or UPFM | Polyamine | Properties of the UF Polyamine Color of Liquid | Viscosity at 25° C. in Poises |
|---|---|---|---|---|
| 6 | 130 g. UFM of Example 1 = 72 g. non-volatile = 1.5 equivalents | 155 g. diethylene triamine 1.5 moles | water white transparent | 1.2 |
| 7 | 260 g. UFM of Example 1 = 143 g. non-volatile = 3 equivalents | 206 g. diethylene triamine 2.0 moles | water white transparent | 2.15 |
| 8 | 85 g. UFM of Example 1 = 47.5 g. non-volatile = 1 equivalent | 146 g. triethylene tetramine 1.0 mole | light yellow transparent | 2.4 |
| 9 | 167 g. UFM of Example 1 = 92 g. non-volatile = 1.93 equivalents | 486 g. 70% solution of hexamethylene diamine in H$_2$O = 340 g. non-volatile = 2.93 moles | water white transparent; when cooled to 15° C., some white crystals formed but melted at 25° C. | about 1 |
| 10 | 260 g. UFM of Example 1 = 144 g. non-volatile = 3.04 equivalents | 500 g. 70% solution of hexamethylene diamine in H$_2$O = 350 g. non-volatile = 3.20 moles | water white transparent | 3.4 |
| 11 | 170 g. UFM of Example 1 = 95 g. non-volatile = 2.0 equivalents | 100 g. Jeffamine D-400 (polyoxypropylene diamine MW 400) = 0.25 mole / 290 g. 70% solution of hexamethylene diamine in H$_2$O = 203 g. non-volatile = 1.75 moles | water white transparent | 1.8 |
| 12 | 85 g. UFM of Example 1 = 47.5 g. non-volatile = 1 equivalent | 230 g. Jeffamine D-230 polyoxypropylene diamine MW 230 | very slightly yellow transparent | 3.3 |
| 13 | 170 g. UFM of Example 1 = 95 g. non-volatile = 2 equivalents | 122 g. monoethanol amine = 2 moles | light yellow transparent | 11.2 |
| 14 | 200 g. UPFM of Example 3 urea-nonyl phenol formaldehyde monomer = 94 g. non-volatile = 1.2 equivalents | 164 g. 85% solution of hexamethylene diamine in H$_2$O = 140 g. non-volatile = 1.2 moles | light yellow transparent | about 1.5 |
| 15 | 160 g. UPFM of Example 3 = 77 g. non-volatile = 1.0 equivalent | 160 g. Adogen 572 (oleyl diamine) = 1.0 equivalent | light tan-yellow translucent | 1.1 |
| 16 | 300 g. UPFM of Example 4 = 150 g. non-volatile | 300 g. 70% solution of hexamethylene diamine in H$_2$O | light yellow transparent | about 1.5 |

TABLE 1-continued

| Example No. | UFM or UPFM | Polyamine | Properties of the UF Polyamine | |
|---|---|---|---|---|
| | | | Color of Liquid | Viscosity at 25° C. in Poises |
| 17 | 65 g. UFM of Example 1<br>= 36 g. non-volatile<br>= 0.75 equivalent | 300 g. Jeffamine T403<br>(polyoxypropylene triamine MW 400)<br>0.75 mole | water-white<br>sl. cloudy | 10.8 |
| 18 | 43 g. UFM of Example 1<br>= 24 g. non-volatile<br>= 0.5 equivalent | 300 g. Jeffamine ED-600<br>[poly(oxyethylene)diamine]<br>mol. wt. 600 | water-white<br>transparent | 11 |
| 19 | 172 g. UFM of Example 1<br>= 95 g. non-volatile<br>= 2 equivalents | 340 g. isophorone diamine<br>= two moles<br>a product of Huels,<br>formerly Veba | water-white<br>transparent | 33 |
| 20 | 172 g. UFM of Example 1<br>= 95 g. non-volatile<br>= 2 equivalents | 316 g. trimethyl<br>hexamethylene diamine<br>= two moles<br>a product of Huels<br>formerly Veba | very light yellow<br>transparent | 3.8 |
| 21 | 85 g. UFM of Example 1<br>= 47.5 g. non-volatile<br>= 1.0 equivalent | 129 g. N—aminoethyl piperazine<br>= one mole | water-white<br>transparent | 3.15 |
| 22 | 130 g. UFM of Example 1<br>= 71 g. non-volatile<br>= 1.5 equivalents | 171 g. of water white distillate prepared from du Pont DACH, a mixture of about half 1,2,diamine cyclohexane, about one-quarter hexamethylene diamine, and remainder of related compounds including 1,5 aminomethyl pentane diamine. The original material is very dark, but the distillate is water white. | water-white<br>transparent | 3.0 |
| 23 | 107 g. thiourea-formaldehyde monomer in methanol, Example 2<br>= 51.5 g. non-volatiles<br>= 1.0 equivalent | 166 g. 70% hexamethylene diamine in water<br>= 116 g. 100% HMD<br>= 1.0 mole | water-white<br>transparent | 4.0 |
| 24 | 85 g. UFM<br>= 47.5 g. non-volatile<br>= 1 equivalent | 136 g. m-xylene diamine<br>= 1 mole | water-white<br>transparent | — |

EXAMPLES OF CURE OF EPOXY RESINS

The various urea-formaldehyde type polyamines were reacted with the standard epoxy resin—the diglycidyl ether of bisphenol A.

The curing reactions were all begun at room temperature, with the resulting exotherm uncontrolled.

The polyamine-to-epoxy-resin ratios shown in the examples below are only approximately stoichiometric and illustrate the curing ability of these new curing agents. For optimum results, one should vary the illustrated ratios in each instance and study the properties of the resulting films or castings, to arrive at the desired property or properties, or to achieve a desired compromise. These properties may be hardness, flexibility, chemical resistance, etc., obtaining either a maximum of one of these or the desired best overall aggregation of properties, for maximum results for one property does not necessarily mean maximum results for another property; so there may not be any one ratio at which the best results for all properties coincide.

TABLE II

| Example No. | UF Polyamine Per Example | Reactants and Proportions | Epoxy Curing Results | Properties of Cured Resin |
|---|---|---|---|---|
| 25 | diethylene triamine Example 6 | 30 g. - liquid epoxy resin, Dow DER 331<br>13 g. - curing agent of Example 6 | Clear transparent mix at once.<br>Exothermed very hot in 40 minutes. | Film on steel very tough |
| 26 | diethylene triamine Example 7 | Same as 25 above | Same as 25 above | Same as 25 above, but perhaps harder film |
| 27 | triethylene tetramine Example 8 | 50 g. DER 331<br>10 g. curing agent of Example 8 | Slightly cloudy mix at once.<br>Exotherm hot in 40 minutes | Very tough film |
| 28 | hexamethylene diamine Example 9 | 30 g. DER 331<br>10 g. of curing agent of Example 9 amine } 15° C. | Very transparent mix at once.<br>Exotherm very, very hot in 45 minutes. | |
| 29 | hexamethylene diamine Example 10 | Same as 28 above | Same as 28 above | |
| 30 | polyoxypropylene diamine MW 400 | 30 g. DER 331<br>15 g. curing agent of Example 11 | Clear transparent mix. Mild exotherm | Excellent, transparent tough, fairly flexible, |

TABLE II-continued

| Example No. | UF Polyamine Per Example | Reactants and Proportions | Epoxy Curing Results | Properties of Cured Resin |
|---|---|---|---|---|
| 31 | Example 11 polyoxypropylene diamine MW 230 Example 12 | 30 g. DER 331, 15 g. curing agent of Example 12 | in about 4 hours. Transparent mix. Slow but positive cure at room temperature. | glossy film. |
| 32 | monoethanol amine Example 13 | 30 g. DER 331, 15 g. of curing agent of Example 13 | Hazy mix, cured in 24 hours. | Soft solid. |
| 33 | hexamethylene diamne Example 14 | 30 g. DER 331, 15 g. of curing agent of Example 14 | Very hot exotherm in 40 minutes | Excellent film on steel. |
| 34 | oleyl diamine Example 15 | 30 g. DER 331, 30 g. of curing agent of Example 15 | Made transparent mix at once. Mix applied to steel panel under water. Film cured under water in 24 hours. | |
| 35 | hexamethylene diamine Example 16 | 53 g. DER 331 18 g. of curing agent of Example 16 } 15° C. | Mix transparent at once. Very hot exotherm in 35 minutes. Applied to steel panel. Set to solid film in 2 hours. | In 24 hours the film was glossy, transparent and very tough and hard. |
| 36 | polyoxypropylene triamine MW 400 Example 17 | 15 g. DER 331, 30 g. of curing agent of Example 17 } 18° C. | | |
| 37 | poly (oxyethylene) diamine MW 600 Example 18 | 30 g. DER 331, 20 g. of curing agent of Example 18 | Very transparent water-white mix at once | Very slow cure. Formed a soft casting in 10 days |
| 38 | isophorone diamine Example 19 | 50 g. DER 331, 20 g. of curing agent of Example 19 | Made transparent mix at once. Water-white. Hot exotherm in 60 minutes | |
| 39 | trimethyl hexamethylene diamine Example 20 | 50 g. DER 331, 20 g. of curing agent of Example 20 | Made transparent mix at once. Exotherm of 70° C. in 90 minutes. | |
| 40 | N—amino ethyl piperazine Example 21 | 60 g. DER 331, 30 g. of curing agent of Example 21 | Made transparent mix at once. Very hot exotherm in 40 minutes. | Made hard film on an aluminum panel. |
| 41 | 1,2 diamine cyclohexane Example 22 | 30 g. DER 331, 15 g. of curing agent of Example 22 | Made transparent mix at once. Hot exotherm in 40 minutes | Made hard film on an aluminum panel. |
| 42 | 2,4 bis (p-aminobenzyl) aniline Example 5 | 20 g. DER 331, 10 g. of curing agent of Example 5 5 g. benzyl alcohol | Transparent dark brown-red liquid on mixing, cured to hard casting in 24 hours. | Made excellent hard transparent glossy adhesive film on steel and on aluminum in 24 hours. |
| 43 | hexamethylene diamine Example 23 | 50 g. DER 331 20 g. of curing agent of Example 23 | Mix transparent at once. Hot exotherm in 35 minutes. | |
| 44 | m-xylene diamine Example 24 | 50 g. DER 331, 20 g. of curing agent of Example 24 | Mix transparent at once. Hot exotherm in 35 minutes. | |

The invention having been described and exemplified what I claim as my invention is:

1. The reaction product of epoxy resin with

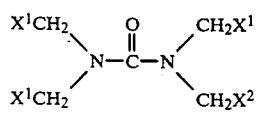

where $X^1$ is

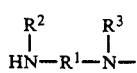

and $X^2$ is $X^1$ or

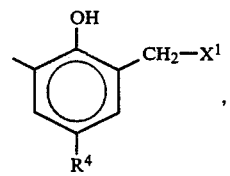

where $R^1$ is one of the following:

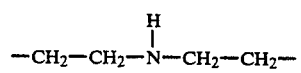 (a)

-continued

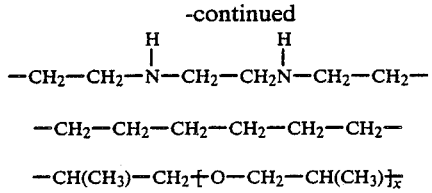

x varying from about 2 to about 6

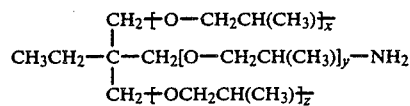

where x+y+z=about 5.3

where a+c=3.5 and b=13.5

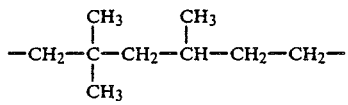

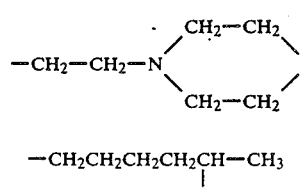

—CH₂CH₂CH₂CH₂CH—CH₃

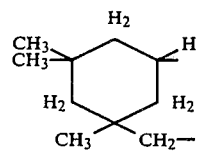

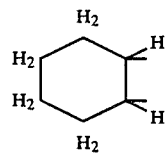

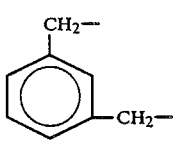

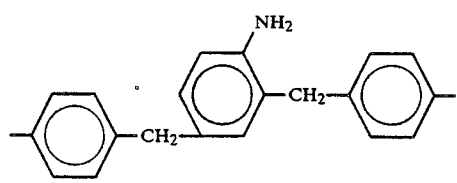

mixture of

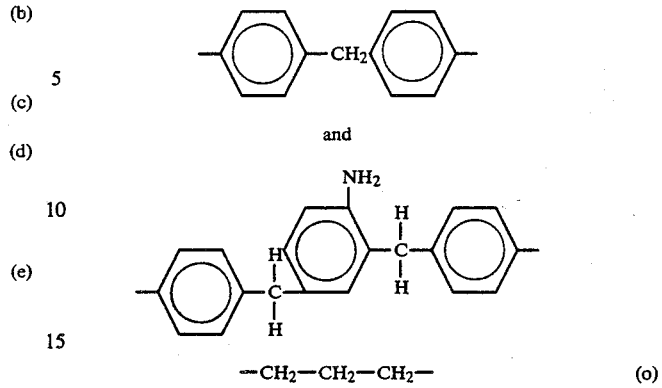

—CH₂—CH₂—CH₂— (o)

$R^2$ and $R^3$ are both H where $R^1$ is any of (a) to (l) and when $R^1$ is (o), either $R^2$ or $R^3$, but not both, is $C_{18}H_{35}$, while the other is H, and $R^4$ is H or an alkyl radical with one to nine carbon atoms.

2. The reaction product of diglycidyl ether of bisphenol A with

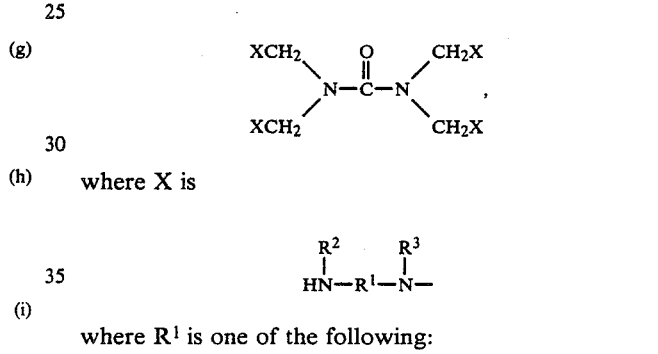

where X is $$\underset{HN-R^1-N-}{\overset{R^2 \quad\quad R^3}{}}$$

where $R^1$ is one of the following:

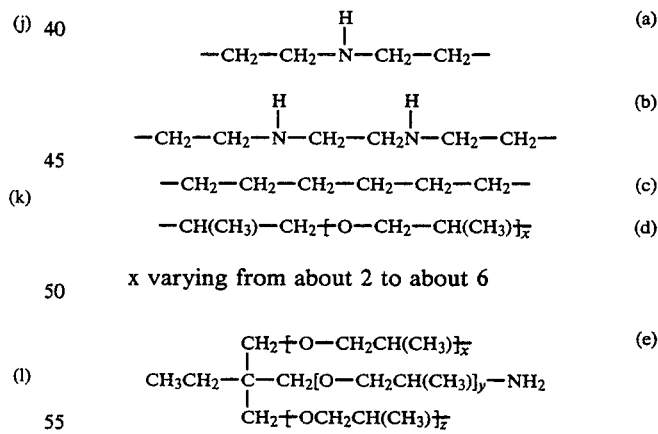

x varying from about 2 to about 6

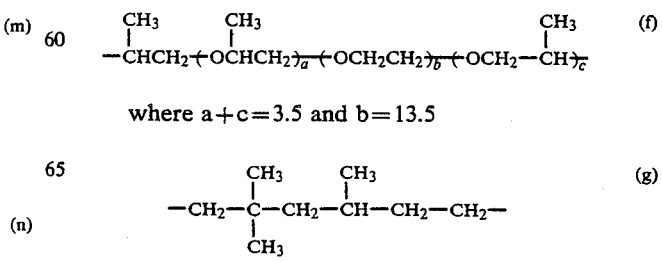

where x+y+z=about 5.3

—CHCH₂(̵OCHCH₂)̵ₐ(̵OCH₂CH₂)̵ᵦ(̵OCH₂—CH)̵ᵧ (f)

where a+c=3.5 and b=13.5

—CH₂—C(CH₃)₂—CH₂—CH(CH₃)—CH₂—CH₂— (g)

-continued

—CH₂—CH₂—N(CH₂—CH₂)₂  (h)

—CH₂CH₂CH₂CH₂CH(CH₃)—  (i)

[cyclohexane structure with CH₃, CH₃, CH₃ and CH₂— substituents]  (j)

[cyclohexane structure]  (k)

[m-xylylene: —CH₂—C₆H₄—CH₂—]  (l)

mixture of

[aminodiphenylmethane structures with NH₂]  (m)

and

[diphenylmethane: —C₆H₄—CH₂—C₆H₄—]  (n)

and R² and R³ are both H.

3. The reaction product of diglycidyl ether of bisphenol A with $$X^1CH_2\text{-}N(CH_2X^1)\text{-}C(=O)\text{-}N(CH_2X^1)\text{-}CH_2X^2$$

where X¹ is $$HN(R^2)\text{-}R^1\text{-}N(R^3)\text{-}$$

and X² is

[2-hydroxy-5-R⁴-benzyl—CH₂—X¹ with OH]  (h)

where R¹ is one of the following:

—CH₂—CH₂—NH—CH₂—CH₂—  (a)

—CH₂—CH₂—NH—CH₂—CH₂—NH—CH₂—CH₂—  (b)

—CH₂—CH₂—CH₂—CH₂—CH₂—CH₂—  (c)

—CH(CH₃)—CH₂+O—CH₂—CH(CH₃)+ₓ  (d)

x varying from about 2 to about 6

$$CH_3CH_2\text{-}C(CH_2\text{+}O\text{-}CH_2CH(CH_3)\text{+}_x)(CH_2[O\text{-}CH_2CH(CH_3)]_y\text{-}NH_2)(CH_2\text{+}OCH_2CH(CH_3)\text{+}_z)$$  (e)

where x+y+z=about 5.3

—CHCH₂+OCHCH₂+ₐ(OCH₂CH₂)ᵦ(OCH₂—CH)_c—  with CH₃ groups  (f)

where a+c=3.5 and b=13.5

—CH₂—C(CH₃)₂—CH₂—CH(CH₃)—CH₂—CH₂—  (g)

—CH₂—CH₂—N(CH₂—CH₂)₂  (h)

—CH₂CH₂CH₂CH₂CH(CH₃)—  (i)

[cyclohexane structure with CH₃, CH₃, CH₃ and CH₂—]  (j)

[cyclohexane structure]  (k)

-continued

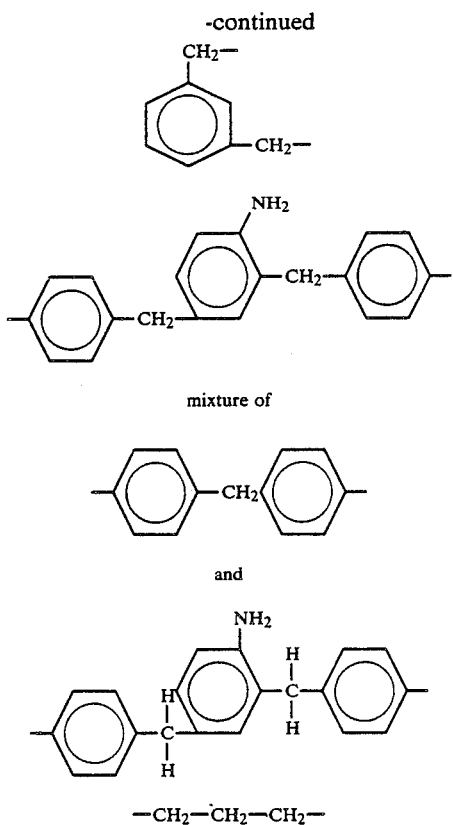

mixture of (n)

and $R^2$ and $R^3$ are both H, and
$R^4$ is H or an alkyl radical with one to nine carbon atoms.

4. The reaction product of diglycidyl ether of bisphenol A with

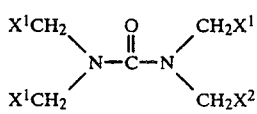

where $X^1$ is

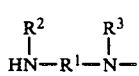

and $X^2$ is $X^1$ or

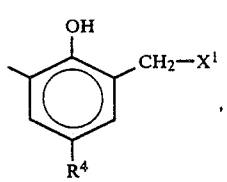

where
$R^1$ is —CH$_2$—CH$_2$—CH$_2$—, either $R^2$ or $R^3$, but not both, being $C_{18}H_{35}$, while the other is H, and
$R^4$ is H or an alkyl radical with one to nine carbon atoms.

5. The reaction product of diglycidyl ether of bisphenol A with

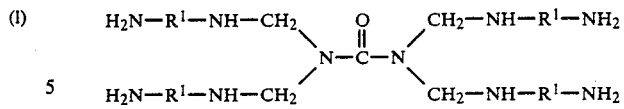

where $R^1$ is

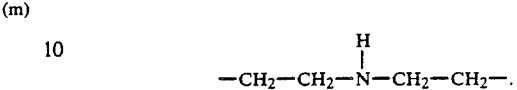

6. The reaction product of diglycidyl ether of bisphenol A with

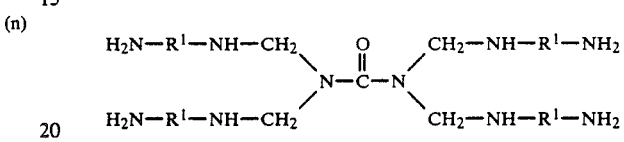

where $R^1$ is

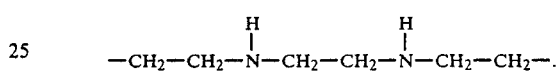

7. The reaction product of diglycidyl ether of bisphenol A with

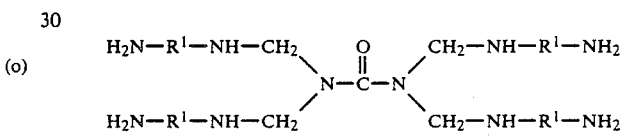

where $R^1$ is —CH$_2$—CH$_2$—CH$_2$—CH$_2$—CH$_2$—CH$_2$—.

8. The reaction product of diglycidyl ether of bisphenol A with

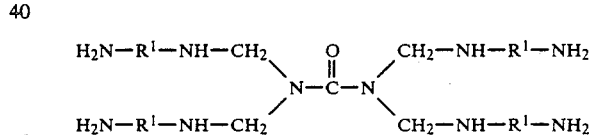

where $R^1$ is

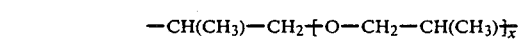

x varying from about 2 to about 6.

9. The reaction product of diglycidyl ether of bisphenol A with

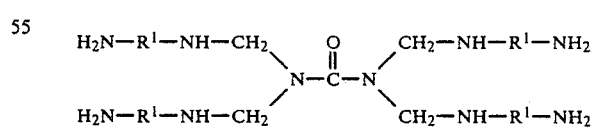

where $R^1$ is

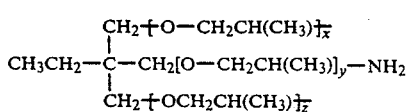

where x+y+z=about 5.3.

10. The reaction product of diglycidyl ether of bisphenol A with $$H_2N-R^1-NH-CH_2 \diagdown \quad O \quad \diagup CH_2-NH-R^1-NH_2$$
$$N-C-N$$
$$H_2N-R^1-NH-CH_2 \diagup \qquad \diagdown CH_2-NH-R^1-NH_2$$

where $R^1$ is $$\begin{matrix} CH_3 & CH_3 & & CH_3 \\ | & | & & | \\ -CHCH_2+OCHCH_2)_{\overline{a}}+OCH_2CH_2)_{\overline{b}}+OCH_2-CH)_{\overline{c}} \end{matrix}$$

where $a+c=3.5$ and $b=13.5$.

11. The reaction product of diglycidyl ether of bisphenol A with $$H_2N-R^1-NH-CH_2 \diagdown \quad O \quad \diagup CH_2-NH-R^1-NH_2$$
$$N-C-N$$
$$H_2N-R^1-NH-CH_2 \diagup \qquad \diagdown CH_2-NH-R^1-NH_2$$

where $R^1$ is $$\begin{matrix} & CH_3 & & CH_3 & & \\ & | & & | & & \\ -CH_2-C-CH_2-CH-CH_2-CH_2-. \\ & | & & & & \\ & CH_3 & & & & \end{matrix}$$

12. The reaction product of diglycidyl ether of bisphenol A with $$HN-R^1-NH-CH_2 \diagdown \quad O \quad \diagup CH_2-NH-R^1-NH$$
$$N-C-N$$
$$HN-R^1-NH-CH_2 \diagup \qquad \diagdown CH_2-NH-R^1-NH$$

where $R^1$ is $$-CH_2-CH_2-N \begin{matrix} CH_2-CH_2 \\ \diagdown \\ \diagup \\ CH_2-CH_2 \end{matrix}$$

13. The reaction product of diglycidyl ether of bisphenol A with $$H_2N-R^1-NH-CH_2 \diagdown \quad O \quad \diagup CH_2-NH-R^1-NH_2$$
$$N-C-N$$
$$H_2N-R^1-NH-CH_2 \diagup \qquad \diagdown CH_2-NH-R^1-NH_2$$

where $R^1$ is $$-CH_2CH_2CH_2CH_2CH-CH_3$$
$$|$$

14. The reaction product of diglycidyl ether of bisphenol A with $$H_2N-R^1-NH-CH_2 \diagdown \quad O \quad \diagup CH_2-NH-R^1-NH_2$$
$$N-C-N$$
$$H_2N-R^1-NH-CH_2 \diagup \qquad \diagdown CH_2-NH-R^1-NH_2$$

where $R^1$ is (cyclohexane ring with substituents $CH_3$, $CH_3$, $H_2$, $H$, $H_2$, $H_2$, $CH_3$, $CH_2-$)

15. The reaction product of diglycidyl ether of bisphenol A with $$H_2N-R^1-NH-CH_2 \diagdown \quad O \quad \diagup CH_2-NH-R^1-NH_2$$
$$N-C-N$$
$$H_2N-R^1-NH-CH_2 \diagup \qquad \diagdown CH_2-NH-R^1-NH_2$$

where $R^1$ is (cyclohexane ring with $H_2$, $H_2$, $H_2$, $H_2$, $H$, $H$ substituents)

16. The reaction product of diglycidyl ether of bisphenol A with $$H_2N-R^1-NH-CH_2 \diagdown \quad O \quad \diagup CH_2-NH-R^1-NH_2$$
$$N-C-N$$
$$H_2N-R^1-NH-CH_2 \diagup \qquad \diagdown CH_2-NH-R^1-NH_2$$

where $R^1$ is (benzene ring with two $CH_2-$ groups in meta position)

17. The reaction product of diglycidyl ether of bisphenol A with $$H_2N-R^1-NH-CH_2 \diagdown \quad O \quad \diagup CH_2-NH-R^1-NH_2$$
$$N-C-N$$
$$H_2N-R^1-NH-CH_2 \diagup \qquad \diagdown CH_2-NH-R^1-NH_2$$

where $R^1$ is (structure with three phenyl rings connected by $CH_2$ groups with an $NH_2$ substituent)

18. The reaction product of diglycidyl ether of bisphenol A with $$H_2N-R^1-NH-CH_2 \quad\quad CH_2-NH-R^1-NH_2$$
$$\phantom{H_2N-R^1-NH-CH}N-\overset{O}{\underset{\|}{C}}-N$$
$$H_2N-R^1-NH-CH_2 \quad\quad CH_2-NH-R^1-NH_2$$

where $R^1$ is a mixture of

—⟨phenyl⟩—CH₂—⟨phenyl⟩— and

—⟨phenyl⟩—CH(H)—⟨phenyl(NH₂)⟩—CH(H)—⟨phenyl⟩—

19. A cured epoxy resin comprising the reaction product of diglycidyl ether of bisphenol A with the reaction product of about four moles of an aliphatic, cycloaliphatic, or aromatic polyamine with about one mole of a monomer of (a) urea-formaldehyde ether, (b) phenolic substituted urea-formaldehyde ether, or (c) thiourea-formaldehyde ether, in which the ether group of the ether molecule is split and a carbon-nitrogen bond to an amine group is formed at the site of the ether splitting.

20. A cured epoxy resin comprising the reaction product of diglycidyl ether of bisphenol A with the reaction product of about four moles of an aliphatic polyamine with one mole of a monomer of (a) urea-formaldehyde ether, (b) phenolic substituted urea-formaldehyde ether, or (c) thiourea formaldehyde ether, in which the ether group of the ether molecule is split and a carbon-nitrogen bond to an amine group is formed at the site of the ether splitting.

21. A cured epoxy resin comprising the reaction product of diglycidyl ether of bisphenol A with the reaction product of about four moles of a cycloaliphatic polyamine with one mole of a monomer of (a) urea-formaldehyde ether (b) phenolic substituted urea-formaldehyde ether, or (c) thiourea formaldehyde ether, in which the ether group of the ether molecule is split and a carbon-nitrogen bond to an amine group is formed at the site of the ether splitting.

22. A cured epoxy resin comprising the reaction product of diglycidyl ether of bisphenol A with the reaction product of about four moles of an aromatic polyamine with one mole of urea-formaldehyde ether monomer, in which the ether group of the ether molecule is split and a carbon-nitrogen bond to an amine group is formed at the site of the ether splitting.

23. A method of curing epoxy resins, comprising reacting an uncured epoxy resin at ambient temperature with $$X^1CH_2 \quad\quad CH_2X^1$$
$$\phantom{X^1CH}N-\overset{O}{\underset{\|}{C}}-N$$
$$X^1CH_2 \quad\quad CH_2X^2$$

where $X^1$ is $$HN-R^1-N-$$
$$\phantom{HN}|\phantom{-R^1-}|$$
$$\phantom{HN}R^2\phantom{-R^1-}R^3$$

and $X^2$ is $X^1$ or

⟨phenyl with OH, CH₂—X¹, and R⁴ substituents⟩ where $R^1$ is one of the following:

(a) $-CH_2-CH_2-\underset{H}{N}-CH_2-CH_2-$ (b) $-CH_2-CH_2-\underset{H}{N}-CH_2-CH_2\underset{H}{N}-CH_2-CH_2-$ (c) $-CH_2-CH_2-CH_2-CH_2-CH_2-CH_2-$ (d) $-CH(CH_3)-CH_2+O-CH_2-CH(CH_3)\overline{)_x}$ x varying from about 2 to about 6

(e) 
$$CH_3CH_2-\underset{\underset{CH_2+OCH_2CH(CH_3)\overline{)_z}}{\overset{CH_2+O-CH_2CH(CH_3)\overline{)_x}}{|}}}{C}-CH_2[O-CH_2CH(CH_3)]_y-NH_2$$

where x+y+z = about 5.3

(f) $-\overset{CH_3}{\underset{|}{C}}HCH_2+OCHCH_2\overline{)_a}+OCH_2CH_2\overline{)_b}+OCH_2-\overset{CH_3}{\underset{|}{C}}H\overline{)_c}$ where a+c = 3.5 and b = 13.5

(g) $-CH_2-\underset{\underset{CH_3}{|}}{\overset{\overset{CH_3}{|}}{C}}-CH_2-\overset{CH_3}{\underset{|}{C}}H-CH_2-CH_2-$ (h) $-CH_2-CH_2-N\underset{CH_2-CH_2}{\overset{CH_2-CH_2}{\diagup\diagdown}}$ (i) $-CH_2CH_2CH_2CH_2\underset{|}{C}H-CH_3$ (j) ⟨cyclohexyl with CH₃, CH₃ substituents⟩

-continued

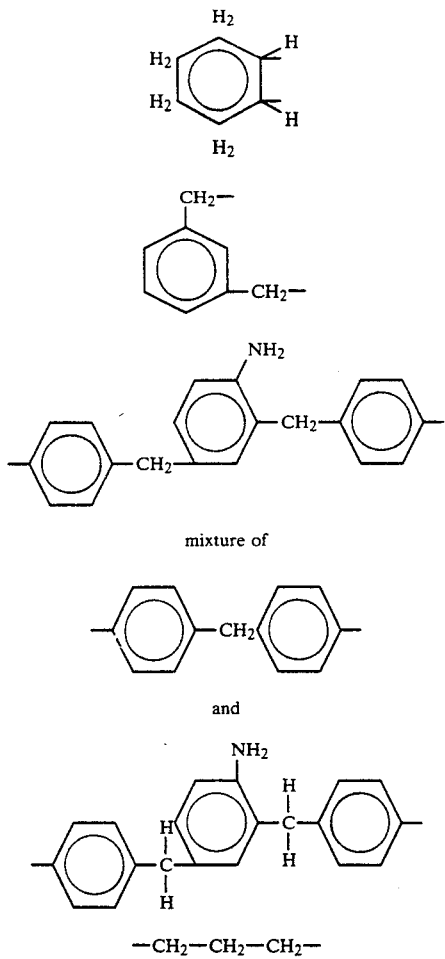

(k)

(l)

(m) mixture of and (n)

—CH₂—CH₂—CH₂— (o)

$R^2$ and $R^3$ are both H where $R^1$ is any of (a) to (l) and when $R^1$ is (m), either $R^2$ or $R^3$, but not both, is $C_{18}H_{35}$, while the other is H, and
$R^4$ is H or an alkyl radical with one to nine carbon atoms.

24. A method of curing epoxy resins, comprising reacting uncured diglycidyl ether of bisphenol A with

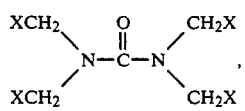

where X is

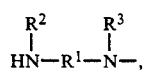

where $R^1$ is one of the following:

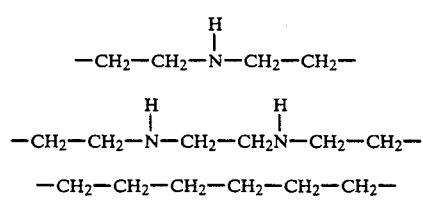

-continued

—CH(CH₃)—CH₂(—O—CH₂—CH(CH₃))ₓ— (d)

x varying from about 2 to about 6

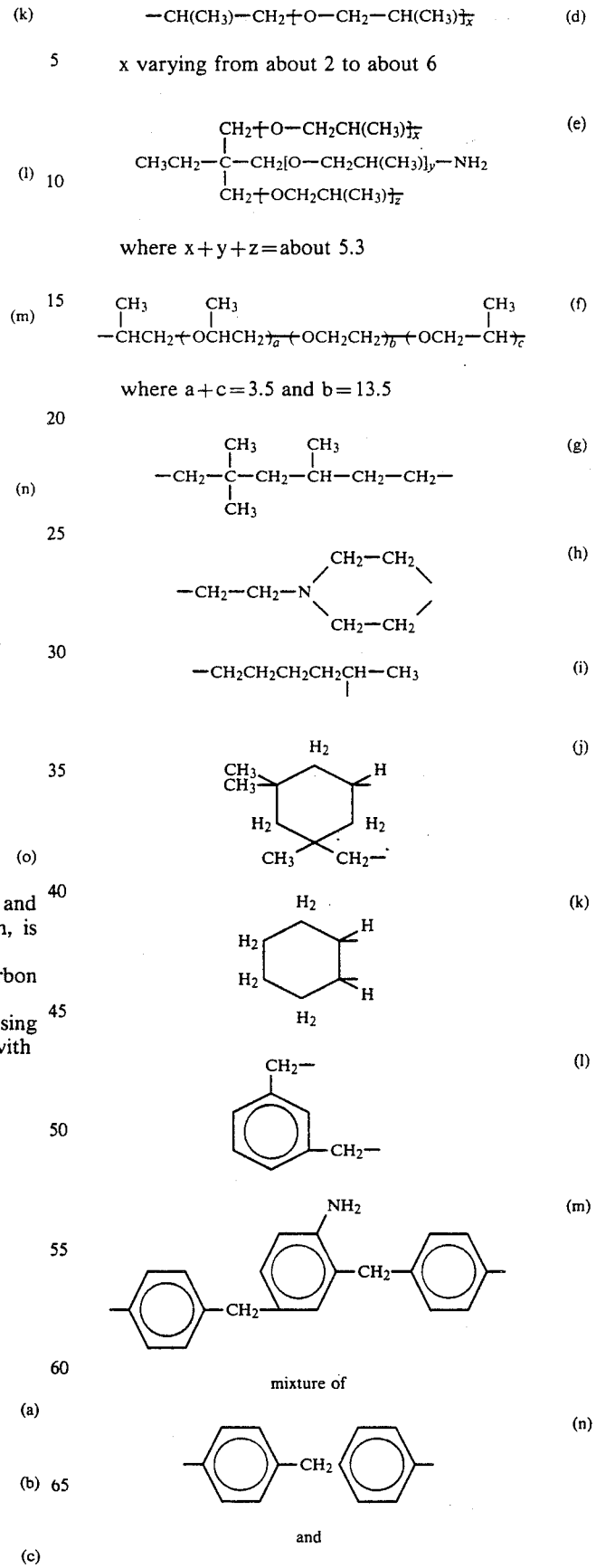

(e)

where x+y+z=about 5.3

(f)

where a+c=3.5 and b=13.5

(g)

(h)

(i)

(j)

(k)

(l)

(m) mixture of (n) and

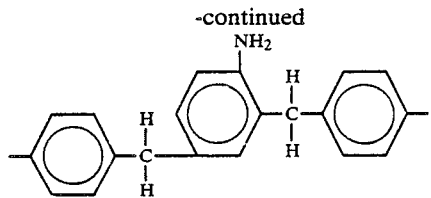

and R² and R³ are both H.

25. A method of curing epoxy resins, comprising reacting uncured diglycidyl ether of bisphenol A with

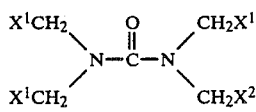

where X¹ is

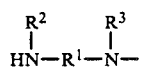

and X² is

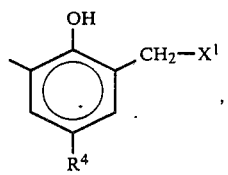

where R¹ is one of the following:

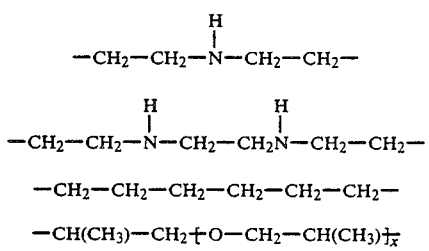

(a)
(b)
(c)
(d)

x varying from about 2 to about 6

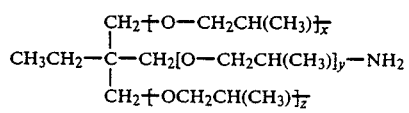

(e)

where x+y+z=about 5.3

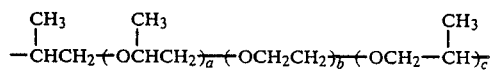

(f)

where a+c=3.5 and b=13.5

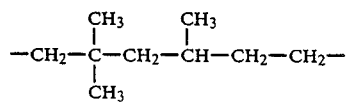

(g)

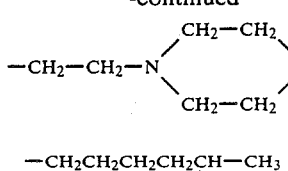

(h)

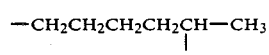

(i)

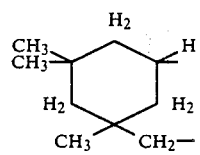

(j)

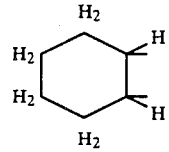

(k)

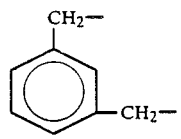

(l)

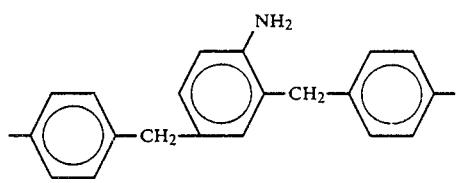

(m)

mixture of

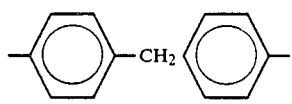

(n)

and

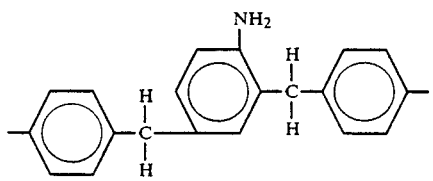

R² and R³ are both H, and
R⁴ is H or an alkyl radical with one to nine carbon atoms.

26. A method of curing epoxy resin, comprising reacting uncured diglycidyl ether of bisphenol A with

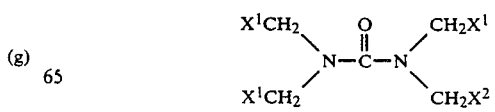

where X¹ is

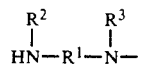

and $X^2$ is $X^1$ or

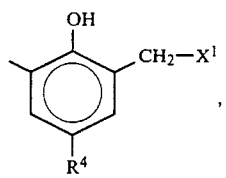

where $R^1$—$CH_2$—$CH_2$—$CH_2$— either $R^2$ or $R^3$, but not both, being $C_{18}H_{35}$, while the other is H, and $R^4$ is H or an alkyl radical with one to nine carbon atoms.

27. A method of curing epoxy resin, comprising reacting uncured diglycidyl ether of bisphenol A with

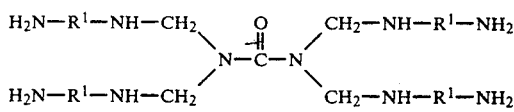

where $R^1$ is

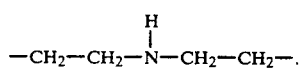

28. A method of curing epoxy resin, comprising reacting uncured diglycidyl ether of bisphenol A with

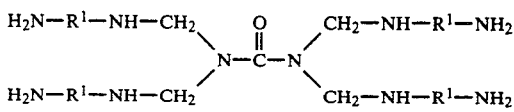

where $R^1$ is

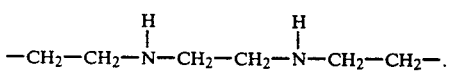

29. A method of curing epoxy resin, comprising reacting uncured diglycidyl ether of bisphenol A with

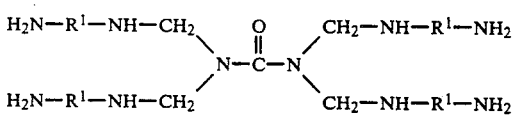

where $R^1$ is —$CH_2$—$CH_2$—$CH_2$—$CH_2$—$CH_2$—$CH_2$—.

30. A method of curing epoxy resin, comprising reacting uncured diglycidyl ether of bisphenol A with

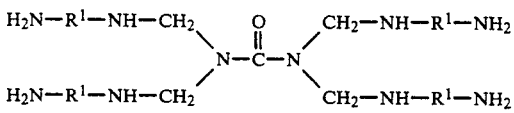

where $R^1$ is

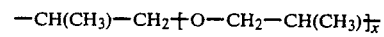

x varying from about 2 to about 6.

31. A method of curing epoxy resin, comprising reacting uncured diglycidyl ether of bisphenol A with

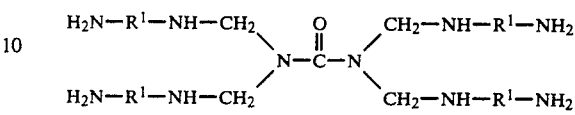

where $R^1$ is

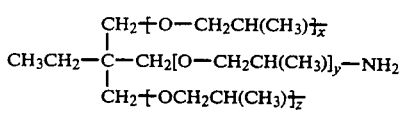

where x+y+z=about 5.3.

32. A method of curing epoxy resin, comprising reacting uncured diglycidyl ether of bisphenol A with

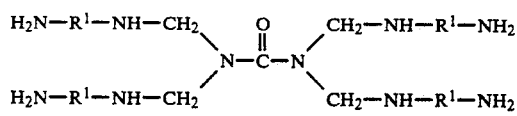

where $R^1$ is

where a+c=3.5 and b=13.5.

33. A method of curing epoxy resin, comprising reacting uncured diglycidyl ether of bisphenol A with

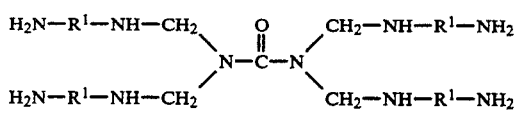

where $R^1$ is

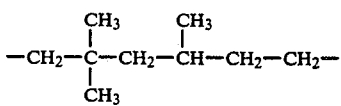

34. A method of curing epoxy resin, comprising reacting uncured diglycidyl ether of bisphenol A with

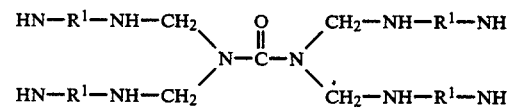

where $R^1$ is

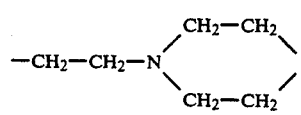

35. A method of curing epoxy resin, comprising reacting uncured diglycidyl ether of bisphenol A with $$H_2N-R^1-NH-CH_2 \diagdown N-\underset{\underset{O}{\overset{\|}{C}}}{} -N \diagup CH_2-NH-R^1-NH_2$$
$$H_2N-R^1-NH-CH_2 \diagup \qquad \diagdown CH_2-NH-R^1-NH_2$$

where $R^1$ is $$-CH_2CH_2CH_2CH_2\underset{|}{CH}-CH_3$$

36. A method of curing epoxy resin, comprising reacting uncured diglycidyl ether of bisphenol A with $$H_2N-R^1-NH-CH_2 \diagdown N-\underset{\underset{O}{\overset{\|}{C}}}{} -N \diagup CH_2-NH-R^1-NH_2$$
$$H_2N-R^1-NH-CH_2 \diagup \qquad \diagdown CH_2-NH-R^1-NH_2$$

where $R^1$ is

[cyclohexane ring with $CH_3$, $CH_3$, $CH_3$, $CH_2-$ substituents]

37. A method of curing epoxy resin, comprising reacting uncured diglycidyl ether of bisphenol A with $$H_2N-R^1-NH-CH_2 \diagdown N-\underset{\underset{O}{\overset{\|}{C}}}{} -N \diagup CH_2-NH-R^1-NH_2$$
$$H_2N-R^1-NH-CH_2 \diagup \qquad \diagdown CH_2-NH-R^1-NH_2$$

where $R^1$ is

[cyclohexane ring]

38. A method of curing epoxy resin, comprising reacting uncured diglycidyl ether of bisphenol A with $$H_2N-R^1-NH-CH_2 \diagdown N-\underset{\underset{O}{\overset{\|}{C}}}{} -N \diagup CH_2-NH-R^1-NH_2$$
$$H_2N-R^1-NH-CH_2 \diagup \qquad \diagdown CH_2-NH-R^1-NH_2$$

where $R^1$ is

[benzene ring with two $CH_2-$ groups]

39. A method of curing epoxy resin, comprising reacting uncured diglycidyl ether of bisphenol A with $$H_2N-R^1-NH-CH_2 \diagdown N-\underset{\underset{O}{\overset{\|}{C}}}{} -N \diagup CH_2-NH-R^1-NH_2$$
$$H_2N-R^1-NH-CH_2 \diagup \qquad \diagdown CH_2-NH-R^1-NH_2$$

where $R^1$ is

[diphenylmethane structure with $NH_2$ group]

40. A method of curing epoxy resin, comprising reacting uncured diglycidyl ether of bisphenol A with $$H_2N-R^1-NH-CH_2 \diagdown N-\underset{\underset{O}{\overset{\|}{C}}}{} -N \diagup CH_2-NH-R^1-NH_2$$
$$H_2N-R^1-NH-CH_2 \diagup \qquad \diagdown CH_2-NH-R^1-NH_2$$

where $R^1$ is a mixture of

[diphenylmethane structure]

and

[diphenylmethane structure with $NH_2$ group]

41. A method of curing epoxy resin, comprising reacting uncured diglycidyl ether of bisphenol A with the reaction product of about four moles of an aliphatic, cycloaliphatic, or aromatic polyamine with one mole of a monomer of (a) urea-formaldehyde ether, (b) a phenolic substituted monomer of urea-formaldehyde ether, or (c) a monomer of thiourea-formaldehyde ether, in which the ether group of the ether molecule is split and a carbon-nitrogen bond to an amine group is formed at the site of the ether splitting.

42. A method of curing epoxy resin, comprising reacting uncured diglycidyl ether of bisphenol A with the reaction product of about four moles of an aliphatic polyamine with one mole of a monomer of (a) urea-formaldehyde ether, (b) phenolic substituted urea-formaldehyde ether, or (c) thiourea-formaldehyde ether, in which the ether group of the ether molecule is split and a carbon-nitrogen bond to an amine group is formed at the site of the ether splitting.

43. A method of curing epoxy resin, comprising reacting uncured diglycidyl ether of bisphenol A with the reaction product of about four moles of a cycloaliphatic polyamine with one mole of a monomer of (a) urea-formaldehyde ether, (b) phenolic substituted urea-formaldehyde ether, or (c) thiourea-formaldehyde ether, in which the ether group of the ether molecule is split and a carbon-nitrogen bond to an amine group is formed at the site of the ether splitting.

44. A method of curing epoxy resin, comprising reacting uncured diglycidyl ether of bisphenol A with the reaction product of about four moles of an aromatic polyamine with one mole of a urea-formaldehyde ether monomer, in which the ether group of the ether molecule is split and a carbon-nitrogen bond to an amine group is formed at the site of the ether splitting.

45. The reaction product of the composition of claim 1 with diglycidyl ether of bisphenol A.

46. The reaction product of (1) the reaction product obtained by reacting about four moles of monoethanol amine with one mole of a monomer of urea-formaldehyde ether, to split the ether group of said urea-formaldehyde ether molecule and form a carbon-nitrogen bond to an amine group at the site of the ether splitting, with (2) diglycidyl ether of bisphenol A.

47. A method for curing epoxy resin comprising the steps of:

(a) reacting urea and paraformaldehyde in a lower alcohol under basic conditions and under heat well below boiling of the alcohol and well above room temperature, (b) adding acid to make the reaction stsrongly acidic, with resulting exotherm, (c) holding the reaction at about 70°–120° C. for about an hour, and (d) bringing the pH to about 7.0, (e) removing the resulting urea-formaldehyde ether monomer from the remaining material, (f) reacting one mole of the urea-formaldehyde ether monomer with about four moles of monoethanol amine to split the ether group of the urea-formaldehyde ether molecule and form a carbon-nitrogen bond to an amine group at the site of the ether splitting, (g) reacting the product resulting from step (f) with uncured diglycidyl either of bisphenol A.

* * * * *